United States Patent
Meng et al.

(10) Patent No.: US 11,905,540 B2
(45) Date of Patent: Feb. 20, 2024

(54) ***CORYNEBACTERIUM* FOR PRODUCING L-LYSINE BY FERMENTATION**

(71) Applicant: NINGXIA EPPEN BIOTECH CO., LTD, Ningxia (CN)

(72) Inventors: Gang Meng, Ningxia (CN); Aiying Wei, Ningxia (CN); Fengyong Ma, Ningxia (CN); Huiping Jia, Ningxia (CN); Jiyin Ma, Ningxia (CN)

(73) Assignee: NINGXIA EPPEN BIOTECH CO., LTD, Yongning (CN)

( * ) Notice: Subject to any disclaimer, the term of this patent is extended or adjusted under 35 U.S.C. 154(b) by 23 days.

(21) Appl. No.: 17/558,582

(22) Filed: Dec. 21, 2021

(65) Prior Publication Data
US 2022/0112529 A1    Apr. 14, 2022

Related U.S. Application Data

(62) Division of application No. 16/329,765, filed as application No. PCT/CN2017/070629 on Jan. 9, 2017, now Pat. No. 11,242,545.

(30) Foreign Application Priority Data

Sep. 1, 2016  (CN) .......................... 201610800567.6
Sep. 1, 2016  (CN) .......................... 201610800601.X

(51) Int. Cl.
| | |
|---|---|
| *C12P 13/08* | (2006.01) |
| *C12N 15/77* | (2006.01) |
| *C12N 1/20* | (2006.01) |
| *C12N 15/74* | (2006.01) |
| *C12R 1/15* | (2006.01) |

(52) U.S. Cl.
CPC ................ *C12P 13/08* (2013.01); *C12N 1/20* (2013.01); *C12N 15/74* (2013.01); *C12N 15/77* (2013.01); *C12N 1/205* (2021.05); *C12R 2001/15* (2021.05)

(58) Field of Classification Search
CPC ........... C12P 13/08; C12N 1/20; C12N 15/74; C12N 15/77; C12N 1/205; C12R 2001/15; C07K 14/34
See application file for complete search history.

(56) References Cited

FOREIGN PATENT DOCUMENTS

WO    WO 2018040469 A1 *  8/2017

OTHER PUBLICATIONS

Carmo Felix et al. (L-lysine production improvement: a review of the state of the art and patent landscape focusing on strain development and fermentation. Technologies. Critical Reviews in Biochemistry (2019), 39(8): 1031-1055). (Year: 2019).*

* cited by examiner

*Primary Examiner* — Iqbal H Chowdhury

(57) ABSTRACT

A method for producing L-lysine by fermentation, comprising modifying a gene for coding an NCBI reference sequence NP_601029.1 and/or NP_599350.1 on a *Corynebacterium* bacterial chromosome to enable the activity and/or expression quantity of NP_601029.1 and/or NP_599350.1 to be reduced; replacing a promoter of one or more genes on the *Corynebacterium* bacterial chromosome with a EP5 promoter, and fermenting bacteria obtained by modification to produce L-lysine. Also provided are methods and applications derived from the method, and bacteria and promoter that can used in the methods and the applications.

12 Claims, No Drawings
Specification includes a Sequence Listing.

SEQUENCE LISTING

```
<160> NUMBER OF SEQ ID NOS: 42

<210> SEQ ID NO 1
<211> LENGTH: 84
<212> TYPE: PRT
<213> ORGANISM: Corynebacterium glutamicum

<400> SEQUENCE: 1

Met Ser Gln Ala Arg Arg Tyr Leu Val Gln Asp Arg Gly Val Ser Leu
1               5                   10                  15

Ser Asp Ala Asp Gly Val Leu Val Asp Leu Asn Phe Thr Cys Thr Gln
            20                  25                  30

Val Asn Glu Ser Asn Asp Thr Asp Leu Ser Val Phe Cys Ser Thr
        35                  40                  45

Ala Ile Ala Gly Lys Asp Pro Ser Glu Leu Arg Lys Glu Leu Glu Ala
    50                  55                  60

Glu Phe Tyr Phe Leu Pro Asp Gly Ala Asp Asp Ala Asp Asp Ala Asp
65                  70                  75                  80

Asp Ala Met Gly

<210> SEQ ID NO 2
<211> LENGTH: 255
<212> TYPE: DNA
<213> ORGANISM: Corynebacterium glutamicum

<400> SEQUENCE: 2
ctagcccatt gcatcgtctg catcgtctgc atcgtctgca ccgtccggca aaaatagaa      60 ttctgcttct agctctttcc gtaattcgga cggatctttt ccagcgatgg cggtactaca    120 gaaacagat agatcatctg tgtcgttaga ctcattaacc tgggtgcatg tgaaattgag     180
atccactaaa acaccatcag catcgctgag ggaaacccct cgatcctgga caaggtatct    240
gcgcgcttga gacat                                                     255

<210> SEQ ID NO 3
<211> LENGTH: 183
<212> TYPE: PRT
<213> ORGANISM: Corynebacterium glutamicum

<400> SEQUENCE: 3

Met Lys Asn Ala Lys Leu Phe Leu Ala Leu Ile Ser Ala Pro Leu Ile
1               5                   10                  15

Leu Ala Gly Cys Ser Ser Thr Asp Thr Gly Thr Ala Glu Ser Thr Ile
            20                  25                  30

Ser Ser Glu Thr Ala Ser Ala Val Asp Ala Thr Thr Ser Thr Ser Ser
        35                  40                  45

Ser Thr Ala Thr Ser Ala Val Ile Asp Asp Pro Val Phe Asp Ile
    50                  55                  60

Ile Asp Ile Val Leu Ala Gln Tyr Pro Asp Arg Ile Ile Thr Asp Ile
```

```
                65                  70                  75                  80
Asp Arg Glu Asp Ser Ser Asp Gln Tyr Glu Val Asp Val Val Gly
                    85                  90                  95

Gln Glu Val Leu Glu Leu Asp Val Thr Thr Ser Gly Gln Ile His Thr
                100                 105                 110

Asp Asp Arg Asp Asn Asp Asp Asp Asp Ile Arg Glu Ala His Ala
            115                 120                 125

Ala Thr Val Thr Ala Ala Gln Ala Ile Gly Leu Ala Leu Asp Gln Tyr
        130                 135                 140

Pro Asp Gly Ile Ile Asp Ser Val Glu Leu Asp Glu Asp Gly Gln
145                 150                 155                 160

Leu Lys Trp Lys Ile Asp Leu Asp Thr Ser Gly Asn Asp Leu Ala
                165                 170                 175

Asp Val Glu Ile Ala Ala Val
            180

<210> SEQ ID NO 4
<211> LENGTH: 552
<212> TYPE: DNA
<213> ORGANISM: Corynebacterium glutamicum

<400> SEQUENCE: 4
ttaaactgct gcgatttcaa cgtcagcaag atcattgccg aagtgtcat cgaggtctat      60 tttccatttc agctggccgt cgtcttcgtc taattcaaca gaatcaataa ttccgtctgg    120
gtattgatcc agcgctaggc caatggcttg agctgcggtg actgtggctg cgtgagcttc    180
gcggatgtcg tcatcatcat cgttgtcgcg gtcgtcggta tggatctggc cactggtggt    240
gacatcaagt tcaaggactt cttggccaac cacaacatcg acttcgtatt gatcggagga    300
gtcttcgcgg tcaatgtcgg tgatgatcct gtcggggtat gggcaagga cgatgtcgat     360 gatgtcgaat accggatcgt catcaatcac ggcagaggtg gcggtacttg aggaggtaga    420
agtggtggca tctactgcag aagcagtttc gctggaaatg gtggattctg ctgttccagt    480
atcggtggag ctgcagccag cgaggataag aggagcggat atgagcgcga ggaaaagttt    540
tgcgttcttc at                                                        552

<210> SEQ ID NO 5
<211> LENGTH: 445
<212> TYPE: DNA
<213> ORGANISM: Artificial Sequence
<220> FEATURE:
<223> OTHER INFORMATION: EP5 promoter

<400> SEQUENCE: 5
cgaggttaag tgtattttag gtgaacaaat ttcagcttcg ggtagaagac cttcgatgcg     60
cttcagagct tctattggga aatctgatac cacttgatta aatagcctac ccccgaattg    120
ggggattggt cattttttgc tgtgaaggta gttttgatgc atatgacctg cgtttataaa    180
gaaatgtaaa cgtgatcaga tcgatataaa agaaacagtt tgtactcagg tttgaagcat    240
tttctccgat tcgcctggca aaaatctcaa ttgtcgctta cagttttcct caacgacagg    300
ctgctaagct gctagttcgg tggcctagtg agtggcgttt acttggataa agtaatccc     360 atgtcgtgat cagccatttt gggttgtttc catagcaatc caaaggtttc gtctttcgat    420
acctattcaa ggagccttcg cctct                                          445

<210> SEQ ID NO 6
```

```
<211> LENGTH: 26
<212> TYPE: DNA
<213> ORGANISM: Artificial Sequence
<220> FEATURE:
<223> OTHER INFORMATION: primer P1

<400> SEQUENCE: 6
cccaagcttc gacagggctt ggattg                                        26

<210> SEQ ID NO 7
<211> LENGTH: 40
<212> TYPE: DNA
<213> ORGANISM: Artificial Sequence
<220> FEATURE:
<223> OTHER INFORMATION: primer P2

<400> SEQUENCE: 7
atggagaaat acgtcaaggt ttttcctgct ctttaacacc                         40

<210> SEQ ID NO 8
<211> LENGTH: 40
<212> TYPE: DNA
<213> ORGANISM: Artificial Sequence
<220> FEATURE:
<223> OTHER INFORMATION: primer P3

<400> SEQUENCE: 8
ggtgttaaag agcaggaaaa accttgacgt atttctccat                         40

<210> SEQ ID NO 9
<211> LENGTH: 26
<212> TYPE: DNA
<213> ORGANISM: Artificial Sequence
<220> FEATURE:
<223> OTHER INFORMATION: primer P4

<400> SEQUENCE: 9
cgggatcccg gtgggtttgt tgatgt                                        26

<210> SEQ ID NO 10
<211> LENGTH: 20
<212> TYPE: DNA
<213> ORGANISM: Artificial Sequence
<220> FEATURE:
<223> OTHER INFORMATION: primer P5

<400> SEQUENCE: 10
ggtagtccca catcatctct                                               20

<210> SEQ ID NO 11
<211> LENGTH: 17
<212> TYPE: DNA
<213> ORGANISM: Artificial Sequence
<220> FEATURE:
<223> OTHER INFORMATION: primer P6

<400> SEQUENCE: 11
atgccctggt tggttct                                                  17

<210> SEQ ID NO 12
<211> LENGTH: 29
<212> TYPE: DNA
<213> ORGANISM: Artificial Sequence
<220> FEATURE:
<223> OTHER INFORMATION: primer P7

<400> SEQUENCE: 12
```
cccaagcttc gcagcaggta tgtagtcac                                    29

<210> SEQ ID NO 13
<211> LENGTH: 40
<212> TYPE: DNA
<213> ORGANISM: Artificial Sequence
<220> FEATURE:
<223> OTHER INFORMATION: primer P8

<400> SEQUENCE: 13
cacttcatag ggttgaatac agcacgcgca cggaaagcca                        40

<210> SEQ ID NO 14
<211> LENGTH: 40
<212> TYPE: DNA
<213> ORGANISM: Artificial Sequence
<220> FEATURE:
<223> OTHER INFORMATION: primer P9

<400> SEQUENCE: 14
tggctttccg tgcgcgtgct gtattcaacc ctatgaagtg                        40

<210> SEQ ID NO 15
<211> LENGTH: 26
<212> TYPE: DNA
<213> ORGANISM: Artificial Sequence
<220> FEATURE:
<223> OTHER INFORMATION: primer P10

<400> SEQUENCE: 15
gctctagagc gggcatccac aatcat                                       26

<210> SEQ ID NO 16
<211> LENGTH: 19
<212> TYPE: DNA
<213> ORGANISM: Artificial Sequence
<220> FEATURE:
<223> OTHER INFORMATION: primer P11

<400> SEQUENCE: 16
aactgggctc ttgttactg                                               19

<210> SEQ ID NO 17
<211> LENGTH: 17
<212> TYPE: DNA
<213> ORGANISM: Artificial Sequence
<220> FEATURE:
<223> OTHER INFORMATION: primer P12

<400> SEQUENCE: 17
cgctgccgct tcacgat                                                 17

<210> SEQ ID NO 18
<211> LENGTH: 450
<212> TYPE: DNA
<213> ORGANISM: Artificial Sequence
<220> FEATURE:
<223> OTHER INFORMATION: sequencing result

<400> SEQUENCE: 18
gtaacccgag gttaagtgta ttttaggtga acaaatttca gcttcgggta gaagaccttc    60
gatgcgcttc agagcttcta ttgggaaatc tgataccact tgattaaata gcctaccccc   120
gaattggggg attggtcatt ttttgctgtg aaggtagttt tgatgcatat gacctgcgtt   180

```
tataaagaaa gtaaacgtga tcagatcgat ataaaagaaa cagtttgtac tcaggtttga    240
agcattttct ccgattcgcc tggcaaaaat ctcaattgtc gcttacagtt tttctcaacg    300
acaggctgct aagctgctag ttcggtggcc tagtgagtgg cgtttacttg gataaaagta    360
atcccatgtc gtgatcagcc attttgggtt gtttccatag caatccaaag gtttcgtctt    420
tcgataccta ttcaaggagc cttcgcctct                                     450
```

```
<210> SEQ ID NO 19
<211> LENGTH: 27
<212> TYPE: DNA
<213> ORGANISM: Artificial Sequence
<220> FEATURE:
<223> OTHER INFORMATION: primer P13

<400> SEQUENCE: 19
gctctagacg tagccaacga agtaatc                                        27

<210> SEQ ID NO 20
<211> LENGTH: 47
<212> TYPE: DNA
<213> ORGANISM: Artificial Sequence
<220> FEATURE:
<223> OTHER INFORMATION: primer P14

<400> SEQUENCE: 20
ctattcaagg agccttcgcc tctatgacca acatccgcgt agctatc                  47

<210> SEQ ID NO 21
<211> LENGTH: 47
<212> TYPE: DNA
<213> ORGANISM: Artificial Sequence
<220> FEATURE:
<223> OTHER INFORMATION: primer P15

<400> SEQUENCE: 21
gatagctacg cggatgttgg tcatagaggc gaaggctcct tgaatag                  47

<210> SEQ ID NO 22
<211> LENGTH: 49
<212> TYPE: DNA
<213> ORGANISM: Artificial Sequence
<220> FEATURE:
<223> OTHER INFORMATION: primer P16

<400> SEQUENCE: 22
caattttgga ggattacaag aacgtaaccc gaggttaagt gtattttag                49

<210> SEQ ID NO 23
<211> LENGTH: 49
<212> TYPE: DNA
<213> ORGANISM: Artificial Sequence
<220> FEATURE:
<223> OTHER INFORMATION: primer P17

<400> SEQUENCE: 23
ctaaaataca cttaacctcg ggttacgttc ttgtaatcct ccaaaattg                49

<210> SEQ ID NO 24
<211> LENGTH: 26
<212> TYPE: DNA
<213> ORGANISM: Artificial Sequence
<220> FEATURE:
<223> OTHER INFORMATION: primer P18

<400> SEQUENCE: 24
```
cggaattctt tcgggcggca atatag                                          26

<210> SEQ ID NO 25
<211> LENGTH: 26
<212> TYPE: DNA
<213> ORGANISM: Artificial Sequence
<220> FEATURE:
<223> OTHER INFORMATION: primer P19

<400> SEQUENCE: 25
cggaattccc gcaagcagcc acattc                                          26

<210> SEQ ID NO 26
<211> LENGTH: 48
<212> TYPE: DNA
<213> ORGANISM: Artificial Sequence
<220> FEATURE:
<223> OTHER INFORMATION: primer P20

<400> SEQUENCE: 26
ctaaaataca cttaacctcg ggttacctttt gtgcaccttt cgatctac                  48

<210> SEQ ID NO 27
<211> LENGTH: 48
<212> TYPE: DNA
<213> ORGANISM: Artificial Sequence
<220> FEATURE:
<223> OTHER INFORMATION: primer P21

<400> SEQUENCE: 27
gtagatcgaa aggtgcacaa aggtaacccg aggttaagtg tattttag                  48

<210> SEQ ID NO 28
<211> LENGTH: 48
<212> TYPE: DNA
<213> ORGANISM: Artificial Sequence
<220> FEATURE:
<223> OTHER INFORMATION: primer P22

<400> SEQUENCE: 28
catatttctg tacgaccagg gccagagagg cgaaggctcc ttgaatag                  48

<210> SEQ ID NO 29
<211> LENGTH: 48
<212> TYPE: DNA
<213> ORGANISM: Artificial Sequence
<220> FEATURE:
<223> OTHER INFORMATION: primer P23

<400> SEQUENCE: 29
ctattcaagg agccttcgcc tctctggccc tggtcgtaca gaaatatg                  48

<210> SEQ ID NO 30
<211> LENGTH: 28
<212> TYPE: DNA
<213> ORGANISM: Artificial Sequence
<220> FEATURE:
<223> OTHER INFORMATION: primer P24

<400> SEQUENCE: 30
cccaagcttg tggtgccgtc ttctacag                                        28

<210> SEQ ID NO 31
<211> LENGTH: 26
<212> TYPE: DNA

<213> ORGANISM: Artificial Sequence
<220> FEATURE:
<223> OTHER INFORMATION: primer P25

<400> SEQUENCE: 31
cggaattccg aggtaggttc cgtagg                                    26

<210> SEQ ID NO 32
<211> LENGTH: 47
<212> TYPE: DNA
<213> ORGANISM: Artificial Sequence
<220> FEATURE:
<223> OTHER INFORMATION: primer P26

<400> SEQUENCE: 32
ctaaaataca cttaacctcg ggttacgggg agaaattcta gccgagg             47

<210> SEQ ID NO 33
<211> LENGTH: 47
<212> TYPE: DNA
<213> ORGANISM: Artificial Sequence
<220> FEATURE:
<223> OTHER INFORMATION: primer P27

<400> SEQUENCE: 33
cctcggctag aatttctccc cgtaacccga ggttaagtgt attttag             47

<210> SEQ ID NO 34
<211> LENGTH: 46
<212> TYPE: DNA
<213> ORGANISM: Artificial Sequence
<220> FEATURE:
<223> OTHER INFORMATION: primer P28

<400> SEQUENCE: 34
gttgcgagat cagctggtgt catagaggcg aaggctcctt gaatag              46

<210> SEQ ID NO 35
<211> LENGTH: 46
<212> TYPE: DNA
<213> ORGANISM: Artificial Sequence
<220> FEATURE:
<223> OTHER INFORMATION: primer P29

<400> SEQUENCE: 35
ctattcaagg agccttcgcc tctatgacac cagctgatct cgcaac              46

<210> SEQ ID NO 36
<211> LENGTH: 27
<212> TYPE: DNA
<213> ORGANISM: Artificial Sequence
<220> FEATURE:
<223> OTHER INFORMATION: primer P30

<400> SEQUENCE: 36
cccaagcttg ccctcgtttt cgtacag                                   27

<210> SEQ ID NO 37
<211> LENGTH: 27
<212> TYPE: DNA
<213> ORGANISM: Artificial Sequence
<220> FEATURE:
<223> OTHER INFORMATION: primer P31

<400> SEQUENCE: 37
cccaagcttt cgcctgcgtt ccattcc                                   27

```
<210> SEQ ID NO 38
<211> LENGTH: 47
<212> TYPE: DNA
<213> ORGANISM: Artificial Sequence
<220> FEATURE:
<223> OTHER INFORMATION: primer P32

<400> SEQUENCE: 38
ctattcaagg agccttcgcc tctatgccgt caagtacgat caataac        47

<210> SEQ ID NO 39
<211> LENGTH: 47
<212> TYPE: DNA
<213> ORGANISM: Artificial Sequence
<220> FEATURE:
<223> OTHER INFORMATION: primer P33

<400> SEQUENCE: 39
gttattgatc gtacttgacg gcatagaggc gaaggctcct tgaatag        47

<210> SEQ ID NO 40
<211> LENGTH: 47
<212> TYPE: DNA
<213> ORGANISM: Artificial Sequence
<220> FEATURE:
<223> OTHER INFORMATION: primer P34

<400> SEQUENCE: 40
cgattttgct gacaccgggc tgtaacccga ggttaagtgt attttag        47

<210> SEQ ID NO 41
<211> LENGTH: 47
<212> TYPE: DNA
<213> ORGANISM: Artificial Sequence
<220> FEATURE:
<223> OTHER INFORMATION: primer P35

<400> SEQUENCE: 41
ctaaaataca cttaacctcg ggttacagcc cggtgtcagc aaaatcg        47

<210> SEQ ID NO 42
<211> LENGTH: 27
<212> TYPE: DNA
<213> ORGANISM: Artificial Sequence
<220> FEATURE:
<223> OTHER INFORMATION: primer P36

<400> SEQUENCE: 42
cggaattctg cgctgggttg ttatctg        27
```

CORYNEBACTERIUM FOR PRODUCING L-LYSINE BY FERMENTATION

CROSS-REFERENCE TO RELATED APPLICATIONS

This application is a divisional application of U.S. patent application Ser. No. 16/329,765 filed on Feb. 28, 2019, which is a U.S. national phase application of PCT application No. PCT/CN2017/070629 filed on Jan. 9, 2017, which in turn claims the priority of Chinese patent application Nos. 201610800601.X and 201610800567.6 both filed on Sep. 1, 2016. The entire content of the aforementioned applications is hereby incorporated by reference.

REFERENCE TO SEQUENCE LISTING

The Sequence Listing is submitted concurrently with the specification as an ASCII formatted text file via EFS-Web, with a file name of "Sequence_listing.TXT", a creation date of Dec. 21, 2021, and a size of 12,232 bytes. The Sequence Listing filed via EFS-Web is part of the specification and is incorporated in its entirety by reference herein.

FIELD OF INVENTION

The present invention belongs to the field of amino acid fermentation, particularly, the present invention relates to methods and applications for producing L-lysine by fermentation, and bacteria and promoters and the like which can be used in such methods and applications.

PRIOR ARTS

The production of L-lysine by fermentation of L-lysine-producing bacteria (e.g., *Escherichia coli* and coryneform bacteria of *Corynebacterium*) has been industrially applied. These bacteria can be bacteria isolated from nature, obtained by mutagenesis or genetic engineering, or both.

The L-lysine-producing bacteria include *Corynebacterium* bacteria. The genetically engineered *Corynebacterium* bacteria of the present invention are mainly obtained by increasing or decreasing the enzyme activity or expression related to the L-lysine metabolic pathway. For example, Chinese Patent CN1017906B has disclosed a L-lysine producing method, which comprises a step of fermentation using a *Corynebacterium* bacterium containing a recombinant DNA for synthesizing a dihydrodipyridine carboxylic acid synthase and/or a succinyltetrahydropyridine carboxylic acid synthase. Chinese patent application CN1187539A has disclosed a L-lysine producing method, which comprises a step of fermentation using a *Corynebacterium* bacterium containing a recombinant DNA. The recombinant DNA encodes an aspartokinase and a diaminopimelate decarboxylase. Chinese patent application CN1310234A has disclosed a L-lysine producing method, which comprises a step of fermentation using a *Corynebacterium* bacterium containing the gene of α-ketoglutarate dehydrogenase. Chinese Patent Application CN1890372A discloses L-lysine producing method, comprising a step of fermentation of *Corynebacterium glutamicum* by increasing the activity of fructose-1,6-bisphosphatase. Chinese patent application CN101065484A has disclosed that a *Corynebacterium* bacterium, which is able to produce L-amino acids, is modified to reduce the activity of acetyl Coenzyme A hydrolase. Chinese patent application CN104245921A has disclosed a L-lysine producing method, which comprises a step of fermentation using *Corynebacterium* bacteria containing a gene encoding xylose isomerase and a gene encoding xylulose kinase. Chinese Patent Application CN101855357A has disclosed a L-lysine producing method, which comprises a step of fermentation using *Corynebacterium glutamicum* that has a mutation on the ptsF gene of fructose-PTS enzyme. Chinese Patent Application CN104245921A has disclosed a L-lysine producing method, which comprises a step of fermentation using a *Corynebacterium* bacterium that contains genes of xylose isomerase and xylulokinase. The entire content of the aforementioned patent application is hereby incorporated by reference.

The aforementioned literatures relating to the production of L-lysine are based on enzymes or genes with known biological function. In the sequenced whole genome of the *Corynebacterium glutamicum* ATCC 13032 (see NCBI Reference Sequence: NC_003450.3), there are 3057 genes. However, among these genes, there are about 1196 genes encoding "hypothetical proteins" whose biological functions are still unclear except those genes with well-defined biological functions. Among these "hypothetical proteins", 236 gene-encoded proteins that have been annotated by bioinformatics methods indicated that they are similar to certain proteins or enzymes, or contain certain domains. However, there are still 960 gene-encoding proteins whose biological functions have not been clarified, and their effects in the production of L-lysine by fermentation remain unknown.

In addition to modifying the gene itself, the improvement of promoters can also increase the enzyme activity. However, most of the promoters of *Corynebacterium* bacteria in the prior art are still wild type promoters, such as *Corynebacterium glutamicum* ATCC 13869 strain (see GenBank: CP016335.1, pp. 2531528 to 2531972), CP strain. (See GenBank: CP012194.1, pp. 2575805 to 2576249), ZL-6 strain (see GenBank: CP604062.1, pp. 2560677 to 2561111), *Brevibacterium flavum* ZL-1 (see GenBank: ICP004046. 1, pp. 2569176 to 2569620).

During the long-term research and practice, the inventor has experienced numerous failures. Luckily, the inventor has discovered that the modification of two genes encoding "hypothetical proteins" in the chromosome of *Corynebacterium* can improve the yield of L-lysine. In addition, the inventor also found that an improved promoter can be obtained by mutating two sites of the wild-type promoter of cspB gene. Replacing the wild-type promoter at other positions on the chromosome of *Corynebacterium* bacteria with improved promoter can also enhance the expression of the corresponding gene and ultimately increase the yield of L-lysine. These two findings not only do not conflict with the modification sites on chromosome of existing modified *Corynebacterium* bacteria which can produce large amount of L-lysine, but also improve the effect of fermentation production of L-lysine duplicately, thus can be applied to a variety of bacteria for producing L-lysine by fermentation.

Content of the Present Invention

The technical problem to be solved by the present invention is to provide a new method for producing L-lysine by fermentation and related methods, including a method for improving fermentation production of L-lysine by modified bacteria compared with unmodified bacteria, a use of modified bacteria in producing L-lysine by fermentation, a use of modified bacteria in improving fermentation production of L-lysine compared with unmodified bacteria, and/or a method for modifying bacteria, etc. In addition, the present invention further relates to bacteria obtained by corresponding modification, and promoters used therein and the expression cassettes, vectors, host cells and the like used therein.

Specifically, in the first aspect, the present invention provides a method for producing L-lysine by fermentation, comprising:

(1) modifying a gene or genes encoding NCBI reference sequences NP_601029.1 and/or NP_599350.1 on a chromosome of *Corynebacterium* bacteria to reduce the activity and/or expression of NP_601029.1 and/or NP_599350.1;

(2) optionally replacing a promoter of one or more genes on the bacterial chromosome obtained by step (1) with an EP5 promoter, wherein the gene encodes a protein whose increase in the enzyme activity and/or expression is beneficial for increasing yield of L-lysine, the polynucleotide sequence of the EP5 promoter (a) is shown in SEQ ID NO: 5, or, (b) is a polynucleotide sequence having 90% or more identity to the polynucleotide sequence of SEQ ID NO: 5, which retains promoting activity of the promoter in (a), and the 51st position of which remains as C, and the 88th position of which remains as T; and, (3) fermenting bacteria obtained by step (1) or (2) to produce L-lysine.

As used herein, the term "optionally" can be understood selected or not selected. For example, if the above step (2) is not selected, and then fermentation production of L-lysine is carried out with the modified bacteria obtained by the step (1). Preferably, in the method of the first aspect herein, the aforesaid step (2) is selected, and the L-lysine is produced by the fermentation of modified bacteria obtained by step (2).

As used herein, the term "modification" refers to a change of corresponding modified object to achieve a certain effect. Means for modifying genes located on a chromosome include, but not limited to, mutagenesis, site-directed mutation, and/or homologous recombination, preferably the latter two. The gene located on the chromosome is modified means one or more nucleotides has been added, deleted or substituted, for example, a gene can be inserted by a nonsense codon, or a gene can be knocked out. A gene can also be modified indirectly by modifying the regulatory sequences of the gene to reduce the activity and/or expression of the encoded protein.

These techniques are widely documented in molecular biology and microbiology literature, and many of which have even been commercialized. In a specific embodiment of the present invention, according to the principle of homologous recombination, the pKOV plasmid system commercially available from Addgene can be used for transformation, or the pK18mobsacB plasmid system can be used for transformation. Thus, as used herein, the modification is preferably a modification by homologous recombination, and more preferably knock-out by homologous recombination.

As used herein, the NCBI reference sequence NP_601029.1 (abbreviated as NP_601029.1) is a "hypothetical protein" whose amino acid sequence is shown in SEQ ID NO: 1 (also available from website http://www.ncbi.nlm.nih.gov, NP_601029.1). The (complementary) nucleotide sequence of the gene encoding NP_601029.1 is shown in SEQ ID NO: 2 (also available from NCBI website as NCgl1751). Although the specific activity of NP_601029.1 is still unknown, in a specific embodiment of the present invention, the production of lysine is increased when the NCgl1751 gene is knocked out (i.e., its activity and/or expression is disabled). Therefore, as used herein, preferably disable the activity and/or expression of NP_601029.1.

As used herein, the NCBI reference sequence NP_599350.1 (abbreviated as NP_599350.1) is a "hypothetical protein" whose amino acid sequence is shown in SEQ ID NO: 3 (also available from website of http://www.ncbi.nlm.nih.gov, NP_599350.1). The (complementary) nucleotide sequence of the gene encoding NP_599350.1 is shown in SEQ ID NO: 4 (also available from NCBI website as NCgl0097). Although the specific activity of NP_599350.1 is still unknown, in a specific embodiment of the present invention, the production of lysine is increased when the NCgl0097 gene is knocked out (i.e., its activity and/or expression quantity disappears). Therefore, as used herein, preferably disable the activity and/or expression of NP_599350.1.

In addition, one or more genes' promoter to be replaced is preferably the wild type promoter of the gene or genes. Herein, the wild-type promoter can be defined as a promoter of gene in *Corynebacterium glutamicum* ATCC13032 (whole genome sequence can be obtained from the NCBI website).

As used herein, the gene encodes a protein whose increase of the enzyme activity and/or expression is beneficial for increasing yield of L-lysine. These genes are not limited to those listed in the embodiments and prior art of the invention.

The number of promoter to be replaced may be one or more, preferably several, e.g. 2-6. In the specific embodiments of the present invention the number of promoters to be replaced are 1, 2, 3, and 4, respectively.

The key of the modification of promoter designed by the present inventors is that the 51st position corresponding to SEQ ID NO: 5 remains as C, and the 88th position remains as T, so when the two sites remain unchanged, other positions may have a slight variations including addition, deletion and/or substitution of one and/or several nucleotides. The polynucleotide sequence of the EP5 promoter herein is preferably a polynucleotide having 95% (more preferably 97%, e.g. 98%, 99%) or more identity to the polynucleotide sequence of SEQ ID NO: 5. One skilled in the art can calculate the identity of polynucleotide sequences by conventional procedures such as Blast and FASTA.

Accordingly, the present invention also provides other uses or methods. For example, in the second aspect, the present invention provides a method for improving the production of L-lysine by fermentation, comprising:

(1) modifying the gene or genes for encoding NCBI reference sequences NP_601029.1 and/or NP_599350.1 on a chromosome of *Corynebacterium* bacteria to reduce (preferably disable) the activity and/or expression of NP_601029.1 and/or NP_599350.1;

(2) optionally replacing the promoter of one or more genes on the bacterial chromosome obtained by step (1) with an EP5 promoter, wherein the gene encodes a protein whose increase in the enzyme activity and/or expression is beneficial for increasing the yield of L-lysine, the polynucleotide sequence of the EP5 promoter (a) is shown in SEQ ID NO: 5, or, (b) is a polynucleotide sequence having 90% (preferably 95%, more preferably 97%, e.g. 98%, 99%) or more identity to the polynucleotide sequence of SEQ ID NO: 5, which retains promoting activity of the promoter in (a), and the 51st position of which remains as C, and the 88th position of which remains as T; and, (3) fermenting bacteria obtained by step (1) or (2) to produce L-lysine.

In the third aspect, the present invention provides a use of modified bacteria in producing L-lysine by fermentation, wherein the modified bacteria is obtained by modifying the gene or genes encoding NCBI reference sequence NP_601029.1 and/or NP_599350.1 on the chromosome of a *Corynebacterium* bacteria to reduce (preferably disable) the activity and/or expression of NP_601029.1 and/or NP_599350.1;

and/or, the modified bacteria are obtained by replacing the promoter of one or more genes on the chromosome of *Corynebacterium* bacteria with an EP5 promoter, wherein the gene encodes a protein whose increase in the enzyme activity and/or expression is beneficial for increasing the yield of L-lysine, the polynucleotide sequence of the EP5 promoter
(a) is shown in SEQ ID NO: 5, or,
(b) is a polynucleotide sequence having 90% (preferably 95%, more preferably 97%, such as 98%, 99%) or more identity to the polynucleotide sequence of SEQ ID NO: 5, which retains promoting activity of the promoter in (a), and the 51st position of which remains as C, and the 88th position of which remains as T.

Accordingly, in the fourth aspect, the present invention provides a use of modified bacteria in improving the production of L-lysine by fermentation, wherein the modified bacteria are obtained by modifying the gene encoding NCBI reference sequences NP_601029.1 and/or NP_599350.1 on the chromosome a *Corynebacterium* bacteria to reduce (preferably disable) the activity and/or expression of NP_601029.1 and/or NP_599350.1;

and/or, the modified bacteria are obtained by replacing the promoter of one or more genes on the chromosome of *Corynebacterium* bacteria with an EP5 promoter, wherein the gene encodes a protein whose increase in the enzyme activity and/or expression is beneficial for increasing the yield of L-lysine, the polynucleotide sequence of the EP5 promoter
(a) is shown in SEQ ID NO: 5, or,
(b) is a polynucleotide sequence having 90% (preferably 95%, more preferably 97%, e.g. 98%, 99%) or more identity to the polynucleotide sequence of SEQ ID NO: 5, which retains promoting activity of the promoter in (a), and the 51st position of which remains as C, and the 88th position of which remains as T.

Herein, unless otherwise defined (such as those without being defined by "modified bacteria"), the term "bacteria" or "*Corynebacterium* bacteria" is an unmodified or pre-modified bacteria or *Corynebacterium* bacteria, its chromosome has a wild-type gene encoding NCBI reference sequences NP_601029.1 and/or NP_599350.1, and/or its chromosome has a wild-type promoter on one or more genes to be modified.

L-lysine is an important metabolite of bacteria, and most *Corynebacterium* bacteria are more or less capable of producing a certain amount of L-lysine by fermentation. The genes encoding the NCBI reference sequences NP_601029.1 and/or NP_599350.1 have not been applied for improving the production/fermentation of lysine, and the promoters of the present invention which replace the promoters at corresponding positions (e.g., GenBank: CP016335.1, pp. 2531528 to 2531972, etc.) have not been applied for improving the production/fermentation of lysine in prior art. So the L-lysine-producing *Corynebacterium* bacteria in the prior art usually have wild-type genes encoding NCBI reference sequence NP_601029.1 and/or NP_599350 with a large number of wild-type promoters, which can basically be modified by the method used herein to improve the production of L-lysine by fermentation. As used herein, the *Corynebacterium* bacteria include *Corynebacterium glutamicum* or *Corynebacterium pekinense*, preferably *Corynebacterium glutamicum*.

Essentially, in the fifth aspect, the present invention provides a method for modifying a bacterium, which comprises a method for modifying a *Corynebacterium* bacteria, comprising the modification of a gene or genes encoding NCBI reference sequence NP_601029.1 and/or NP_599350.1 on a chromosome of *Corynebacterium* bacteria to reduce (preferably disable) the activity and/or expression of NP_601029.1 and/or NP_599350.1;

and/or comprising replacement of the promoter of one or more genes on the chromosome of *Corynebacterium* bacterial with an EP5 promoter, wherein the gene encodes a protein whose increase in the enzyme activity and/or expression is beneficial for increasing yield of L-lysine, the polynucleotide sequence of the EP5 promoter
(a) is shown in SEQ ID NO: 5, or,
(b) is a polynucleotide sequence having 90% (preferably 95%, more preferably 97%, e.g. 98%, 99%) or more identity to the polynucleotide sequence of SEQ ID NO: 5, which retains promoting activity of the promoter in (a), and the 51st position of which remains as C, and the 88th position of which remains as T.

The modified bacteria obtained by the method of the fifth aspect herein can be used for yielding or producing L-lysine by fermentation. Accordingly, in the sixth aspect, the present invention provides a modified bacteria obtained by the method of the fifth aspect herein. The bacteria of the sixth aspect of the invention is *Corynebacterium* bacteria, the corresponding nucleotide sequences of gene locus encoding NCBI reference sequences NP_601029.1 and/or NP_599350.1 on its chromosome are different from that of NP_601029.1 and/or NP_599350, and/or the nucleotide sequences of the gene locus encoding one or more wild-type promoters on its chromosome are substituted with the nucleotide sequence of the EP5 promoter herein. Preferably, the genes encoding the NCBI reference sequences NP_601029.1 and/or NP_599350.1 on the bacterial chromosome of the sixth aspect of the invention are knocked out.

In the seventh aspect, the present invention provides a use of the NCBI reference sequences NP_601029.1 and/or NP_599350.1 and/or their encoding genes in producing L-lysine by fermentation of *Corynebacterium* bacteria. Although the increase of the activity and/or expression of the NCBI reference sequences NP_601029.1 and/or NP_599350.1 may reduce the production of L-lysine by fermentation of *Corynebacterium* bacteria, preferably the use is a use of reducing (preferably disabling, such as knocking out the encoding gene) the activity and/or expression of the NCBI reference sequence NP_601029.1 and/or NP_599350.1, so that improve the production of L-lysine by the fermentation of *Corynebacterium* bacteria. Wherein, the amino acid sequence of the NCBI reference sequence NP_601029.1 is shown in SEQ ID NO: 1, the (complementary) nucleotide sequence of its encoding gene is shown in SEQ ID NO: 2; the amino acid sequence of the NCBI reference sequence NP_599350.1 is shown in SEQ ID NO: 3, and the (complementary) nucleotide sequence of its encoding gene is shown in SEQ ID NO: 4.

In the eighth aspect, the present invention provides an EP5 promoter having a polynucleotide sequence
(a) shown in SEQ ID NO: 5, or
(b) shown 90% (preferably 95%, more preferably 97%, e.g. 98%, 99%) or more identity to the polynucleotide sequence of SEQ ID NO: 5, which retains promoting activity of the promoter in (a), and the 51st position of which remains as C, and the 88th position of which remains as T.

In the ninth aspect, the present invention provides an expression cassette comprising the promoter of the eighth aspect herein and an encoding sequence operably linked to said promoter. As used herein, operably linked means that the encoding sequence is functionally linked to the promoter, typically ligated to the 3' end of the promoter such that the promoter sequence can initiate or mediate transcription of the encoding sequence.

In the tenth aspect, the present invention provides a vector comprising the promoter of the eighth aspect herein and an encoding sequence operably linked to said promoter. The vector is preferably an expression vector.

In the eleventh aspect, the present invention provides a host cell comprising the expression cassette of the ninth aspect or the vector of the tenth aspect herein, or obtained by transforming the expression cassette of the ninth aspect or the vector of the tenth aspect herein. The host cell of the present invention comprises an EP5 promoter. Preferably, the host cell is a Corynebacterium bacterium, such as Corynebacterium glutamicum.

In the twelfth aspect, the present invention provides a use of the promoter of the eighth aspect herein in producing L-lysine by fermentation or improving production of L-lysine by fermentation, preferably the use of the promoter of claim 8 in producing L-lysine by fermentation or improving production of L-lysine by fermentation of Corynebacterium bacteria.

In the thirteenth aspect, the present invention provides a method for screening a gene having an impact on producing L-lysine by fermentation of Corynebacterium bacteria, comprising:
(1) modifying the gene for encoding a "hypothetical protein" on the chromosome of Corynebacterium bacteria to increase or reduce the activity and/or expression of the "hypothetical protein";
(2) fermenting bacteria obtained by step (1) to produce L-lysine; and,
(3) comparing yield of L-lysine obtained by step (2) with yield of L-lysine of unmodified Corynebacterium bacteria.

Preferably, in the method of the thirteenth aspect herein, the impact is increasing yield of L-lysine, and reducing the activity and/or expression of the "hypothetical protein", preferably disabling such as knock-out the gene encoding the "hypothetical protein".

The present invention has the beneficial effects that a new method for improving the fermentation yield of L-lysine is developed and proved in practice, and the method does not conflict with the chromosomal modification sites of existing modified Corynebacterium bacteria which can produce L-lysine with large amount and high yield, which can be used for further increase yield of L-lysine in practice.

In order to facilitate understanding, the present invention will be described in detail below by specific embodiments. It should be particularly pointed out that these descriptions are merely exemplary descriptions and do not limit the scope of the present invention. Many variations and modifications of the present invention will be apparent to those skilled in the art from the discussion in this specification.

In addition, the present invention refers to published literatures, which are all incorporated herein by reference in their entirety, as if their entire content has been described herein.

Biomaterial Collection Information

The *Corynebacterium glutamicum* strain YP097158 of the present invention has been deposited at China General Microbiological Culture Collection Center (CGMCC) on Aug. 16, 2016, and the deposit address of CGMCC is the Institute of Microbiology Chinese Academy Sciences, NO. 3, Yard NO. 1 West Beichen Road, Chaoyang District, Beijing, Zip Code: 100101. The accession number of the strain is CGMCC No. 12856, which was registered and proved to be viable.

DETAILED DESCRIPTION OF THE PREFERRED EMBODIMENT

The following embodiments further illustrate the present invention. Unless otherwise specified, the technical means used in the embodiments are conventional means well known to those skilled in the art and commercially available common instruments and reagents. For reference, please refer to "Molecular Cloning Experiment Guide (3rd Edition)" (Science Press), "Microbiology Experiment (4th Edition)" (Higher Education Press) and manufacturer's instructions for the corresponding instruments and reagents.

Embodiment 1 Down-Regulation of NCgl1751 Gene Expression

According to the genome sequence of *Corynebacterium glutamicum* ATCC13032 published by NCBI, two pairs of primers were synthesized for amplifying two end fragments of the encoding region of NCgl1751 gene as the upstream and downstream homology arm fragments. Primers were designed as follows (synthesized by Shanghai Yingjun Company):

```
P1:
                                        (SEQ ID NO: 6)
5' CCCAAGCTTCGACAGGGCTTGGATTG 3'  (HindIII)

P2:
                                        (SEQ ID NO: 7)
5' ATGGAGAAAT ACGTCAAGGT TTTTCCTGCT CTTTAACACC 3'

P3:
                                        (SEQ ID NO: 8)
5' GGTGTTAAAG AGCAGGAAAA ACCTTGACGT ATTTCTCCAT 3'

P4:
                                        (SEQ ID NO: 9)
5' CGGGATCCCGGTGGGTTTGTTGATGT 3'  (BamHI)
```

Using *Corynebacterium glutamicum* ATCC13032 as a template, and P_1/P2 and P3/P4 as primer pair respectively, PCR amplification were carried out to obtain 660 bp of the upstream homology arm fragment and 780 bp of the downstream homology arm fragment. Then the primers P1/P4 were used for OVER PCR to obtain a 1440 bp of whole homology arm fragment, both ends of which contains Hind III and BamHI restriction sites, respectively. After the PCR reactions, the amplified products were recovered by electrophoresis. The needed 1400 bp of DNA fragment was recovered by a column DNA gel recovery kit, digested by restriction enzyme, and ligated with the shuttle plasmid pk18mobsacB plasmid to obtain a knock-out plasmid. The plasmid contains a kanamycin resistance marker.

The knock-out plasmid was electrotransformed into the patented lysine producing strain YP97136 (the construction method can be referred to WO2014121669A1; the existence of wild type NCgl1751 gene on the chromosome of the strain was confirmed by sequencing). Single colonies produced by culturing were identified by PCR, respectively, using the following primers (synthesized by Shanghai Yingjun Company):

P5:
(SEQ ID NO: 10)
5' GGTAGTCCCACATCATCTCT 3'

P6:
(SEQ ID NO: 11)
5' ATGCCCTGGTTGGTTCT 3'

Strains with bands of 1000 bp and 740 bp amplified by PCR are positive strains, and the strains with only a band of 1000 bp are the original bacteria. Positive strains were cultured on kanamycin-containing medium and kanamycin-free medium, respectively. The strains grown on kanamycin-free medium but not kanamycin-containing medium were further identified by PCR using the P5/P6 primers. Strains amplified with a band of 740 bp is a genetically engineered strains with the encoding region of the Ncgl1751 gene being knocked out, which was named YPL-1-001.

Embodiment 2 Down-Regulation of NCgl0097 Gene Expression

According to the genome sequence of *Corynebacterium glutamicum* ATCC13032 published by NCBI, two pairs of primers were synthesized for amplifying the two end fragments of the encoding region of NCgl0097 gene as the upstream and downstream homology arm fragments. Primers were designed as follows (synthesized by Shanghai Yingjun Company):

P7:
(SEQ ID NO: 12)
5' CCCAAGCTTCGCAGCAGGTATGTAGTCAC 3' (HindIII)

P8:
(SEQ ID NO: 13)
5' CACTTCATAG GGTTGAATAC AGCACGCGCA CGGAAAGCCA 3'

P9:
(SEQ ID NO: 14)
5' TGGCTTTCCG TGCGCGTGCT GTATTCAACC CTATGAAGTG 3'

P10:
(SEQ ID NO: 15)
5' GCTCTAGAGCGGGCATCCACAATCAT 3' (Xba I)

Using *Corynebacterium glutamicum* ATCC13032 as a template, and P7/P8 and P9/P10 as primer pair respectively, PCR amplification were carried out to obtain 740 bp of the upstream homology arm fragment and 640 bp of the downstream homology arm fragment. Then the primers P7/P8 were used for OVER PCR to obtain a 1380 bp of whole homology arm fragment, both ends of which contains Hind III and Xba I restriction sites, respectively. After the PCR reactions, the amplified products were recovered by electrophoresis. The needed 1380 bp of DNA fragment was recovered by a column DNA gel recovery kit, digested by restriction enzyme, and ligated with the shuttle plasmid pk18mobsacB plasmid to obtain a knock-out plasmid. The plasmid contains a kanamycin resistance marker, and a recombinant whose plasmid is integrated into the genome can be selected by kanamycin screening.

The knockout plasmid was electrotransformed into the patented lysine producing strain YP97136 (the existence of wild type NCgl0097 gene on the chromosome of the strain was confirmed by sequencing). Single colonies obtained by culturing were identified by PCR, respectively, using the following primers (synthesized by Shanghai Yingjun Company):

P11:
(SEQ ID NO: 16)
5' AACTGGGCTCTTGTTACTG 3'

P12:
(SEQ ID NO: 17)
5' CGCTGCCGCTTCACGAT 3'

Strains with bands of 1195 bp and 645 bp amplified by PCR are positive strains, and the strains with only one band of 1195 bp are the original bacteria. Positive strains were cultured on kanamycin-containing medium and kanamycin-free medium, respectively. The strains grown on kanamycin-free medium but not kanamycin-containing medium were further identified by PCR using the P11/P12 primers. Strain amplified with a band of 645 bp is a genetically engineered strain with the encoding region of the Ncgl0097 gene being knocked out, which was named YPL-1-002.

Embodiment 3 Down-Regulation of Both NCgl1751 and NCgl0097 Genes Expression

Based on the strain YPL-1-001, the encoding region of the Ncgl0097 gene on the genome was knocked out, and the detailed process of knock-out was the same as the above-mentioned Ncgl0097 gene encoding region. The strain was verified by PCR using the identification primers P5/P6 and P11/P12, and the fragments with size of 740 bp and 645 bp (the size of PCR products from original strains were 1000 bp and 1195 bp, respectively) were obtained. The genetically engineered strain with the encoding regions of NCgl1751 and NCgl0097 genes being knocked out was named YPL-1-003 (also named as YP097158), and deposited at China General Microbiological Culture Collection Center (CGMCC) on Aug. 16, 2016, with an accession number of CGMCC No.12856.

Embodiment 4 Promoter of the Present Invention

According to the promoter having polynucleotide sequence of SEQ ID NO: 5 designed by the present inventors, the corresponding polynucleotide was synthesized and ligated into pMD19-T vector, and the obtained new vector T-EP5 was sequenced (sequenced by Shanghai Yingjun Company) and the result is as follows:

(SEQ ID NO: 18)
GTAACCCGAG GTTAAGTGTA TTTTAGGTGA ACAAATTTCA

GCTTCGGGTA GAAGACcTTCGATGCGCTTC AGAGCTTCTA

TTGGGAAATC TGAtACCACT TGATTAAATA

GCCTACCCCGAATTGGGGG ATTGGTCATT TTTTGCTGTG

AAGGTAGTTT TGATGCATAT GACCTGCGTTTATAAAGAAA

GTAAACGTG ATCAGATCGA TATAAAAGAA ACAGTTTGTA

CTCAGGTTTGAAGCATTTTC TCCGATTCGC CTGGCAAAAA

TCTCAATTGT CGCTTACAGT TTTTCTCAAC GACAGGCTGC

TAAGCTGCTA GTTCGGTGGC CTAGTGAGTG GCGTTTACTT

GGATAAAAGTAATCCCATGT CGTGATCAGC CATTTTGGGT

-continued

TGTTTCCATA GCAATCCAAA GGTTTCGTCTTTCGATACCT

ATTCAAGGAG CCTTCGCCTC T

The sequencing result contains the sequence of promoter shown in SEQ ID NO: 5, indicating that this clone is correct. The promoter sequence designed by the present inventors mainly contains two mutations of T->C and C->T (in lower case) compared with the wild-type promoter, and the sequence of promoter shown in SEQ ID NO: 5 is referred as EP5 below.

Embodiment 5 EP5 Promoter Regulates the Expression of ddh Gene

Based on the sequence of EP5 mentioned-above and the genome sequence of *Corynebacterium glutamicum* ATCC13032 published on NCBI, primers were designed for inserting the EP5 fragment in front of the initiation codon ATG of the ddh gene, so that EP5 can promote the expression of ddh gene. The specific design of primers is as follows:

```
P13:
                                     (SEQ ID NO: 19)
5' GCTCTAGACGTAGCCAACGAAGTAATC 3' (Xba I)

P14:
                                     (SEQ ID NO: 20)
5'CTATTCAAGG AGCCTTCGCC TCTATGACCA ACATCCGCGT

AGCTATC 3'

P15:
                                     (SEQ ID NO: 21)
5'GATAGCTACG CGGATGTTGG TCATAGAGGC GAAGGCTCCT

TGAATAG3'

P16:
                                     (SEQ ID NO: 22)
5'CAATTTTGGA GGATTACAAG AACGTAACCC GAGGTTAAGT

GTATTTTAG3'

P17:
                                     (SEQ ID NO: 23)
5'CTAAAATACA CTTAACCTCG GGTTACGTTC TTGTAATCCT

CCAAAATTG3'

P18:
                                     (SEQ ID NO: 24)
5' CGGAATTCTTTCGGGCGGCAATATAG 3' (EcoR I)
```

A template of *Corynebacterium glutamicum* ATCC13032, primers of P13/P14 and P17/P18 were used for PCR amplification, and 700 bp of the upstream homology arm fragment and 650 bp of the downstream homology arm fragment were obtained. Then primers P15/P16 were used to amplify a 450 bp of EP5 fragment using T-EP5 as a template. Subsequently, the template of a mixture of above three amplified fragments, and the primers of P13/P18 were used to amplify the whole homology arm fragment with both ends of which containing Xba I and EcoR I restriction sites respectively. After the PCR reaction, the amplified products were recovered by electrophoresis, and the needed 1800 bp of DNA fragment was recovered by a column DNA gel recovery kit, digested by restriction enzyme, and ligated with the shuttle plasmid pk18mobsacB plasmid to obtain an integrated plasmid. The plasmid contains a kanamycin resistance marker, so a recombinant whose plasmid has been integrated into the genome can be obtained by kanamycin screening.

The integrated plasmid was electrotransformed into the lysine producing strain YPL-1-003 (the existence of promoter of the wild type ddh gene on the chromosome of the strain was confirmed by sequencing). Single colonies obtained by culturing were identified by PCR using the P15/P18 primers. The strain with a bahnd of 1100 bp amplified by PCR is positive strain, and the strain without that band amplified is the original bacterium. Positive strain was cultured on kanamycin-containing medium and kanamycin-free medium. The strain grown on kanamycin-free medium but not kanamycin-containing medium was further identified by PCR using the P15/P18 primers, and the strain with a band of 1100 bp amplified is a strain whose EP5 has been integrated in front of the initiation codon of the ddh gene, which was named YPL-1-004.

Embodiment 6 EP5 Promoter Regulates the Expression of lysC Gene

Based on the sequence of EP5 mentioned-above and the genome sequence of *Corynebacterium glutamicum* ATCC13032 published on NCBI, primers were designed for inserting the EP5 fragment in front of the initiation codon GTG of the lysC gene, so that EP5 can promote the expression of lysC gene. The specific design of primers is as follows:

```
P19:
                                     (SEQ ID NO: 25)
5'CGGAATTCCCGCAAGCAGCCACATTC 3' (EcoR I)

P20:
                                     (SEQ ID NO: 26)
5'CTAAAATACA CTTAACCTCG GGTTACCTTT GTGCACCTTT

CGATCTAC3'

P21:
                                     (SEQ ID NO: 27)
5'GTAGATCGAA AGGTGCACAA AGGTAACCCG AGGTTAAGTG

TATTTTAG3'

P22:
                                     (SEQ ID NO: 28)
5'CATATTTCTG TACGACCAGG GCCAGAGAGG CGAAGGCTCC

TTGAATAG3'

P23:
                                     (SEQ ID NO: 29)
5'CTATTCAAGG AGCCTTCGCC TCTCTGGCCC TGGTCGTACA

GAAATATG3'

P24:
                                     (SEQ ID NO: 30)
5'CCCAAGCTTGTGGTGCCGTCTTCTACAG 3' (Hind III)
```

A template of *Corynebacterium glutamicum* ATCC13032, and primers of P19/P20 and P23/P24 were used for PCR amplification, and 740 bp of the upstream homology arm fragment and 940 bp of the downstream homology arm fragment were obtained. Then the primers P21/P22 were used to amplify 450 bp of the EP5 fragment using T-EP5 as template. Subsequently, the template of a mixture of above three amplified fragments, and the primers of P19/P24 were used to amplify the whole homology arm fragment with both ends of which containing Hind III and EcoR I restriction sites respectively. After the PCR reaction, the amplified products were recovered by electrophoresis, and the needed 2140 bp of DNA fragment was recovered by a column DNA gel recovery kit, digested by restriction enzyme, and ligated with the shuttle plasmid pk18mobsacB plasmid to obtain an integrated plasmid. The plasmid contains a kanamycin resistance marker, so a recombinant whose plasmid has been integrated into the genome can be selected by kanamycin screening.

The integrated plasmid was electrotransformed into YPL-1-004 (the existence of promoter of the wild type lysC gene on the chromosome of the strain has been confirmed by sequencing). Single colonies produced by culturing were identified by PCR using the P21/P24 primers. The strain with a band of 1400 bp amplified by PCR is positive strains, and the strain without amplified band is the original bacterium. Positive strain was cultured on kanamycin-containing medium and kanamycin-free medium. The strain grown on kanamycin-free medium but not kanamycin-containing medium was further identified by PCR using the P21/P24 primers, and the strain with a band of 1400 bp is a strain whose EP5 has been integrated in front of the initiation codon of the lysC gene, which was named YPL-1-005.

Embodiment 7 EP5 Promoter Regulates the Expression of lysA Gene

Based on the sequence of EP5 mentioned-above and the genome sequence of *Corynebacterium glutamicum* ATCC13032 published on NCBI, primers were designed for inserting the EP5 fragment in front of the initiation codon ATG of the lysA gene, so that EP5 can promote the expression of lysA gene. The specific design of primers is as follows:

```
P25:
                                  (SEQ ID NO: 31)
5' CGGAATTCCGAGGTAGGTTCCGTAGG 3'  ( Eco RI)

P26:
                                  (SEQ ID NO: 32)
5' CTAAAATACA CTTAACCTCG GGTTACGGGG AGAAATTCTA
GCCGAGG 3'

P27:
                                  (SEQ ID NO: 33)
5' CCTCGGCTAG AATTTCTCCC CGTAACCCGA GGTTAAGTGT
ATTTTAG 3'

P28:
                                  (SEQ ID NO: 34)
5' GTTGCGAGAT CAGCTGGTGT CATAGAGGCG AAGGCTCCTT
GAATAG 3'

P29:
                                  (SEQ ID NO: 35)
5' CTATTCAAGG AGCCTTCGCC TCTATGACAC CAGCTGATCT
CGCAAC 3'

P30:
                                  (SEQ ID NO: 36)
5' CCCAAGCTTGCCCTCGTTTTCGTACAG 3' (Hind III)
```

A template of *Corynebacterium glutamicum* ATCC13032, primers of P25/P26 and P29/P30 were used for PCR amplification, and 750 bp of the upstream homology arm fragment and 850 bp of the downstream homology arm fragment were obtained. Then the primers P27/P28 were used to amplify a 450 bp of EP5 fragment using T-EP5 as the template. Subsequently, the template of a mixture of above three amplified fragments, and the primers of P25/P30 were used to amplify the whole homology arm fragment with both ends of which containing Hind III and EcoR I restriction sites respectively. After the PCR reaction, the amplified products were recovered by electrophoresis, and the needed 2050 bp of DNA fragment was recovered by a column DNA gel recovery kit, digested by restriction enzyme, and ligated with the shuttle plasmid pk18mobsacB plasmid to obtain an integrated plasmid. The plasmid contains a kanamycin resistance marker, so a recombinants whose plasmids has been integrated into the genome can be obtained by kanamycin screening.

The integrated plasmid was electrotransformed into YPL-1-005 (the existence of promoter of the wild type lysA gene on the chromosome of the strains has been confirmed by sequencing). Single colonies obtained by culturing were identified by PCR using the P27/P30 primers. The strain with a band of 1300 bp amplified by PCR is positive strain, and the strain without this band amplified is the original bacteria. Positive strain was cultured on kanamycin-containing medium and kanamycin-free medium. The strain grown on kanamycin-free medium but not kanamycin-containing medium was further identified by PCR using the P27/P30 primers, and a strain with a band of 1300 bp amplified is the strain whose EP5 has been integrated into the front end of the initiation codon of the lysA gene, which was named YPL-1-006.

Embodiment 8 EP5 Promoter Regulates the Expression of gnd Gene

Based on the sequence of EP5 mentioned-above and the genomic sequence of *Corynebacterium glutamicum* ATCC13032 published on NCBI, primers were designed for inserting the EP5 fragment in front of the initiation codon ATG of the gnd gene, so that EP5 can promote the expression of gnd gene. The specific design of primers is as follows:

```
P31:
                                  (SEQ ID NO: 37)
5'CCCAAGCTT TCGCCTGCGTTCCATTCC 3' (Hind III)

P32:
                                  (SEQ ID NO: 38)
5'CTATTCAAGG AGCCTTCGCC TCTATGCCGT CAAGTACGAT
CAATAAC 3'

P33:
                                  (SEQ ID NO: 39)
5'GTTATTGATC GTACTTGACG GCATAGAGGC GAAGGCTCCT
TGAATAG3'

P34:
                                  (SEQ ID NO: 40)
5'CGATTTTGCT GACACCGGGC TGTAACCCGA GGTTAAGTGT
ATTTTAG3'

P35:
                                  (SEQ ID NO: 41)
5'CTAAAATACA CTTAACCTCG GGTTACAGCC CGGTGTCAGC
AAAATCG3'

P36:
                                  (SEQ ID NO: 42)
5'CGGAATTC TGCGCTGGGTTGTTATCTG 3' (EcoR I)
```

A template of *Corynebacterium glutamicum* ATCC13032, and primers of P31/P32 and P35/P36 were used for PCR amplification, and 720 bp of the upstream homology arm fragment and 700 bp of the downstream homology arm fragment were obtained. Then the primers P33/P34 were used to amplify a 450 bp of EP5 fragment using T-EP5 as a template. Subsequently, the template of a mixture of above three amplified fragments, and the primers of P31/P36 were used while the mixture of the above three amplified fragments was the template to amplify the whole homology arm fragment with both ends of which containing Hind III and EcoR I restriction sites respectively. After the PCR reaction, the amplified products were recovered by electrophoresis, and the needed 1870 bp of DNA fragment was recovered by a column DNA gel recovery kit, digested by restriction enzyme, and ligated with the shuttle plasmid pk18mobsacB plasmid to obtain an integrated plasmid. The plasmid contains a kanamycin resistance marker, so a recombinant whose plasmid has been integrated into the genome can be obtained by kanamycin screening.

The integrated plasmid was electrotransformed into YPL-1-006 (the existence of promoter of the wild type gnd gene on the chromosome of the strain has been confirmed by sequencing). Single colonies obtained by culturing were identified by PCR using the P33/P36 primers. The strain with a band of 1150 bp amplified by PCR is a positive strain, and the strain without amplified band is the original bacteria. Positive strain was cultured on kanamycin-containing medium and kanamycin-free medium. The strain grown on kanamycin-free medium but not kanamycin-containing medium was further identified by PCR using the P33/P36 primers, and a strain with a band of 1150 bp amplified is the strain whose EP5 has been integrated into the front end of the initiation codon of the gnd gene, which was named YPL-1-007.

Embodiment 9 Lysine Fermentation Experiment

The strains constructed in Embodiments 1-3 and 5-8 and the original strains were used for fermentation experiment in a type of BLBIO-5GC-4-H fermentation tank (purchased from Shanghai Bailun Biotechnology Co., Ltd.) with the medium shown in Table 1 and the process shown in Table 2. Each strain was repeated three times (wherein YPL-1-003 was tested 6 times), and the results are shown in Table 3.

TABLE 1

Formula of fermentation medium

| Product Name | Ratio |
| --- | --- |
| Sugar hydrolyzed from starch | 30 g/L |
| Ammonium sulfate | 12 g/L |
| Magnesium sulfate | 0.87 g/L |
| Molasses | 20 g/L |
| Acidified corn syrup | 3 ml/L |
| Phosphate | 0.4 ml/L |
| Potassium chloride | 0.53 g/L |
| Defoamer (2% Defoamer Polyether) | 4 ml/L |
| Ferrous sulfate | 120 mg/L |
| Manganese sulfate | 120 mg/L |
| Nicotinamide | 42 mg/L |
| Calcium pantothenate | 6.3 mg/L |
| VB1 | 6.3 mg/L |
| Copper and zinc salt solution | 0.6 g/L |
| Biotin | 0.88 mg/L |

TABLE 2

Fermentation process

| | |
| --- | --- |
| Correction DO100% | Temperature 37° C., air volume 4 L/min, rotating speed 1000 rpm, tank pressure 0 mpa, calibration after 5 minutes |
| Inoculation volume | 300 ml    Culture temperature ° C.    37° C. |
| pH | pH 6.9 ± 0.05    Dissolved oxygen DO    10-30% |
| Initial condition | Temperature 37° C., PH 6.9, tank pressure 0 mpa, air volume 3 L/min, rotating speed 550 rpm |
| Full process control | 1. when dissolved oxygen < 30%, increase the rotating speed to 750 rpm→800 rpm→air volume to 4 L/min→850 rpm→950 rpm in turn; 2. after fermentation for 6 h, increase the tank pressure to 0.01 Mpa; after fermentation for 12 h, increase the tank pressure to 0.02 Mpa→0.03 Mpa→0.04 Mpa→0.05 Mpa. |
| Residual sugar control | 0.1-0.2% before F12 h; residual sugar was controlled to 0.1-0.05% combined with DO needs after F12 h. |
| Ammonia & nitrogen control | Before F12 h: 0.1-0.15; F12-F32 h: 0.15-0.25; after F32 h: 0.1-0.15 |
| Fed batch | 25% ammonium hydroxide, 70% concentrated sugar, 50% ammonium sulfate, 10% Defoamer Poly ether |
| Turnaround | About 48 h |

TABLE 3

Results of lysine fermentation experiment (lysine content g/dl)

| Batch | Control YP97136 | YPL-1-001 | YPL-1-002 | YPL-1-003 | YPL-1-004 | YPL-1-005 | YPL-1-006 | YPL-1-007 |
| --- | --- | --- | --- | --- | --- | --- | --- | --- |
| 1 | 18.8 | 20.0 | 20.5 | 21.8 | | | | |
| 2 | 18.6 | 20.1 | 20.6 | 22.2 | | | | |
| 3 | 18.8 | 20.2 | 20.8 | 22.1 | | | | |
| 4 | | | | 22.0 | 23.5 | 24.1 | 24.9 | 25.7 |
| 5 | | | | 22.2 | 23.4 | 24.0 | 24.8 | 25.6 |
| 6 | | | | 22.1 | 23.4 | 24.1 | 24.9 | 25.8 |
| Mean Value | 18.8 | 20.1 | 20.6 | 22.1 | 23.4 | 24.1 | 24.9 | 25.7 |

The results are shown in Table 3. Down-regulation of the expression of NCgl1751 and/or NCgl0097 genes in *Corynebacterium* contributes to the increase in yield of L-lysine. Among them, the synchronously down-regulation of the expression of both NCgl1751 and NCgl0097 genes achieved the greatest improvement of L-lysine production. The insertion of the EP5 promoter in front of the *Corynebacterium* genes whose increase of expression is beneficial to the yield of L-lysine can regulate the expression of these genes, leading to an increase of the yield of L-lysine production.

Moreover, the more EP5 promoters integrated in front of these genes, the more yield of L-lysine increase, indicating the existence of duplicate effect.

While only specific embodiments of the present invention have been described above, those of skill in the art should understood that these are merely provided by way of illustration, and many variations or modifications can be made to these embodiments without departing from the principle and spirit of the invention. Accordingly, the scope of the invention is defined by the appended claims.

What is claimed is:

1. A promoter, wherein the promoter has the polynucleotide sequence of SEQ ID NO: 5.

2. An expression cassette or vector comprising the promoter of claim 1.

3. A host cell, comprising the expression cassette or vector of claim 2, or is obtained by transforming with the expression cassette or vector of claim 2.

4. The host cell of claim 3, which is a *Corynebacterium* bacteria.

5. The host cell of claim 4, wherein the *Corynebacterium* bacteria is *Corynebacterium glutamicum* or *Corynebacterium pekinense*.

6. The host cell of claim 4, wherein one or more promoters of one or more genes on the chromosome of the *Corynebacterium* bacteria are replaced with the promoter having the polynucleotide sequence of SEQ ID NO: 5, and the one or more genes are selected from the group consisting of aspartate kinase gene (lysC), diaminopimelate decarboxylase gene (lysA), D-2-hydroxyisocaproate dehydrogenase gene (ddh), and phosphogluconate dehydrogenase gene (gnd).

7. The host cell of claim 6, wherein 4 promoters of 4 genes on the chromosome of the *Corynebacterium* bacteria are replaced with the promoter having the polynucleotide sequence of SEQ ID NO: 5, and the 4 genes are aspartate kinase gene (lysC), diaminopimelate decarboxylase gene (lysA), D-2-hydroxyisocaproate dehydrogenase gene (ddh), and phosphogluconate dehydrogenase gene (gnd).

8. The host cell of claim 6, wherein a gene encoding NCBI reference sequence NP_601029.1 on the chromosome of the *Corynebacterium* bacteria is knocked out, and the amino acid sequence of NCBI reference sequence NP_601029.1 is shown in SEQ ID NO: 1.

9. The host cell of claim 8, wherein the nucleotide sequence of the gene encoding NCBI reference sequence NP_601029.1 is shown in SEQ ID NO: 2.

10. The host cell of claim 6, wherein a gene encoding NCBI reference sequence NP_599350.1 on the chromosome of the *Corynebacterium* bacteria is knocked out, and the amino acid sequence of NCBI reference sequence NP_599350.1 is shown in SEQ ID NO: 3.

11. The host cell of claim 10, wherein the nucleotide sequence of the gene encoding NCBI reference sequence NP_599350.1 is shown in SEQ ID NO: 4.

12. A method for producing L-lysine by fermentation, comprising a step of fermenting the host cell of claim 6 to produce L-lysine.

* * * * *